United States Patent [19]
Booth et al.

[11] Patent Number: 5,466,676
[45] Date of Patent: Nov. 14, 1995

[54] SATELLITE CELL PROLIFERATION IN ADULT SKELETAL MUSCLE

[75] Inventors: Frank W. Booth, Houston, Tex.; Donald B. Thomason, Memphis, Tenn.; Paul R. Morrison, Indianapolis, Ind.; George M. Stancel, Houston, Tex.

[73] Assignee: Board of Regents, The University of Texas at Austin

[21] Appl. No.: 823,783

[22] Filed: Jan. 23, 1992

Related U.S. Application Data

[63] Continuation of Ser. No. 479,065, Feb. 12, 1990, abandoned.

[51] Int. Cl.$^6$ ................................................ C12N 15/00
[52] U.S. Cl. ............................................ 514/44; 435/172.3
[58] Field of Search ........................ 435/69.1, 172.3, 435/320.1; 935/57, 62; 514/44; 424/93

[56] References Cited

FOREIGN PATENT DOCUMENTS

| | | |
|---|---|---|
| WO89/02468 | 3/1989 | WIPO. |
| WO89/04663 | 6/1989 | WIPO. |
| WO90/06757 | 6/1990 | WIPO. |
| WO90/15863 | 12/1990 | WIPO. |

OTHER PUBLICATIONS

Karpati et al. (1989), Dystrophin is Express in mdx Skeletal Muscle Fibers After Normal Myoblast Implantation., Am. J. Pathol. 135:27–32.
Schultz, E. and Jaryszak, D. (1985), Effects of Skeletal Muscle Regeneration on the Proliferation Potential of Satellite Cells., *Mechanisms of Aging and Development*, 30:63–72.
McGeachie J. K. and Grounds, M. D. (1987), Initiation and duration of muscle precursor replication after mild and severe injury to skeletal muscle of mice., *Cell Tissue Res.*, 248:125–130.
England et al. (1990), Very mild muscular dystrophy associated with the deletion of 46% of dystrophin., *Nature*, 343:180–182.
Gilboa et al. (1986), Transfer and Expression of Cloned Genes Using Retroviral Vectors., *Biotechniques*, 4(6):504–512.
Allbrook, D. (1981), Skeletal Muscle Regeneration, *Muscle and Nerve*, 4:234–245.
Ishiura et al. (1986), Biochemical Aspects of Bupivacaine–Induced Acute Muscle Degradation., *J. Cell Sci.*, 83:197–212.
Mandel, J. L. (1989), Dystrophia The gene and its product., *Nature*, 339:584–586.
Fabrikant (1987), Adaptation of Cell Renewal Systems Under Continuous Irradiation, *Health Physics*, 52(5):561–570.
Kantoff et al. (1986), Retroviral–Mediated Gene Transfer Into Hematopoietic Cells., *Trans. Assoc. Am. Phy.*, 99:92–102.
Williams et al., eds. (1989), Booth, F. W. (author), Physical Activity as a Stimulus to Changes in Gene Expression in Skeletal Muscle., *In: Biological Effects of Physical Activity*, (2):91–104.
Wolfe et al. (1990), Direct Gene Transfer into Mouse Muscle in Vivo., *Science*, 247:1465–8.
Benoit, P. W. and Belt, W. D. (1970), Destruction and regeneration of skeletal muscle after treatment with a local anaesthetic, bupivacaine (Marcaine), *J. Anat.*, 107:547–556.
Hall–Craggs (1974), Rapid Degeneration and Regeneration of a Whole Skeletal Muscle Following Treatment with Bupivacaine (Marcain), *Experimental Neurology*, 43;349–358.
Hwang et al. (1984), Role of Intron–Contained Sequences in Formation of Moloney Murine Leukemia Virus env mRNA., *Molecular and Cellular Biology*, 4(11):2289–2297.
Williams et al. (1984), Introduction of new genetic material into pluripotent haematopoietic stem cells of the mouse., *Nature*, 310(9):476–480.
Anderson, W. F. (1984), Prospects for Human Gene Therapy., *Science*, 226:401–409.
Nonaka et al. (1984), Regenerative Capability of Skeletal Muscle in Chicken Muscular Dystrophy., *Muscle & Nerve*, 7:400–407.
Love et al. (1989), An autosomal transcript in skeletal muscle with homology to dystrophin., *Nature*, 339:55–58.
Darr, K. C. and Schultz, E. (1987), Exercise–induced satellite cell activation in growing and mature skeletal muscle., *J. Appl. Physiol.*, 63(5):1816–1821.
Edwall et al. (1989), Induction of Insulin–Like Growth Factor I Messenger Ribonucleic Acid during Regeneration of Rat Skeletal Muscle., *Endocrinology*, 124(2):820–825.

(List continued on next page.)

*Primary Examiner*—James Martinell
*Attorney, Agent, or Firm*—Denise L. Mayfield

[57] ABSTRACT

Novel methods of retroviral-mediated gene transfer for the in vivo corporation and stable expression of eukaryotic or prokaryotic foreign genes in tissues of living animals is described. More specifically, methods of incorporating foreign genes into mitotically active cells are disclosed. The constitutive and stable expression of *E. coli* β-galactosidase gene under the promoter control of the Moloney murine leukemia virus long terminal repeat is employed as a particularly preferred embodiment, by way of example, establishes the model upon which the incorporation of a foreign gene into a mitotically-active living eukaryotic tissue is based.

Use of the described methods in therapeutic treatments for genetic diseases, such as those muscular degenerative diseases, is also presented. In muscle tissue, the described processes result in genetically-altered satellite cells which proliferate daughter myoblasts which preferentially fuse to form a single undamaged muscle fiber replacing damaged muscle tissue in a treated animal. The retroviral vector, by way of example, includes a dystrophin gene construct for use in treating muscular dystrophy.

The present invention also comprises an experimental model utilizable in the study of the physiological regulation of skeletal muscle gene expression in intact animals.

14 Claims, 2 Drawing Sheets

OTHER PUBLICATIONS

Partridge et al. (1989), Conversion of mdx myofibres from dystrophin–negative to –positive by injection of normal myoblasts., *Nature*, 337(12):176–179.

Grounds, M. D. and McGeachie J. K. (1987), A model of myogenesis in vivo, derived from detailed autoradiographic studies of regenerating skeletal muscle, challenges the concept of quantal mitosis., *Cell Tissue Res.*, 250:563–569.

Wigler et al. (1977), Transfer of Purified Herpes Virus Thymidine Kinase Gene to Cultured Mouse Cells., *Cell*, 1:223–232.

Moore, M. A. S. (1979), Stem Cell Concepts In: *Muscle Regeneration*, pp. 1–7.

Dannenberg (1981), Histochemical Stains for Macrophages in Cell Smears and Tissue Sections: β–Galactosidase, Acid Phosphates, Nonspecific Esterase, Succinic Dehydrogenase, and Cytochrome Oxidase., In: *Methods for Studying Mononuclear Phagocytes*, pp. 375–396.

Florini, J. R. and Magri, K. A. (1989), Effects of growth factors on myogenic differentiation., *American Journal of Physiology*, C701–C703.

Wilson et al. (1990), Correction of CD18–Deficient Lymphocytes by Retrovirus–Mediated Gene Transfer., *Science*, 248:1413–1416.

Wintrobe, et al., eds. (1974) *Diabetes Melitis* In: Harrison's Principles of Internal Medicine, p. 543.

Bigsby et al. (1988), Progesterone and dexamethasone inhibition of uterine epithelial proliferation in two models of estrogen–independent growth., *Am. J. Obstet. Gynecol.*, 158:646–650.

B. N. Fields, eds., *Virology* (1990) Raven Press, pp. 342, 1439.

Turner et al. (1988), Induction of mRNA for IGF–I and –II during growth hormone–stimulated muscle hypertrophy., *Am. J. Physiol.*, 255 (Endocrinol. Metab.) 18:E513–517.

Bell et al. (1980), Sequence of the human insulin gene., *Nature*, 284:26–32.

Price et al. (1987), Lineage analysis in the vertebrate nervous system by retrovirus–mediated gene transfer., *Proc. Natl. Acad. Sci. USA*, 84:156–160.

Rudman et al. (1990), Effects of Human Growth Hormone in Men Over 60 Years Old., *The New England Journal of Medicine*, 323(1):1–6.

Mary Lee Vance (1990), Growth Hormone for the Elderly?, *The New England Journal of Medicine*, 323(1):52–54.

Inder M. Verma (Nov. 1990), Gene Therapy., *Scientific American*, 68–72.

Patent Cooperation Treaty International Search Report (1991) PCT/US91/00941.

Thomason, D. B. and Booth, F. W. (1989), Twenty–ninth Annual Meeting of the American Society of Cellular Biology: In: *Cell Biology*, 109 (No. 4, part 2):263, Abstract No. 1452.

Friedmann, T. (1989), Progress Toward Human Gene Therapy., *Science*, 244(4910):1275–1281.

Reimann et al. (1986), Introduction of a selectable gene into murine T–lymphoblasts by a retroviral vector., *Journal of Immunological Methods*, 89:93–101.

Palmer et al. (1987), Efficient retrovirus–mediated transfer and expression of a human adenosine deaminase gene in diploid skin fibroblasts from an adenosine deaminase–deficient human., *Proc. Natl. Acad. Sci, USA*, 84:1055–1059.

Ewen, C. and J. H. Hendry, (1989) Radiation Research, 118:169–179, "The Radiosensitivity of Kidney Colony–Forming Cells: A Short–Term Assay in Situ in the Mouse".

Fisher, D. R. et al., (1988) Radiation Research 113:40–50, "Long–Term Repair in vivo of Colony–Forming Ability and Chromosomal Injury in X–Irradiated Mouse Hepatocytes".

Greenberger, Joel S. et al., (1988) Int. J. Radiation Oncology Biol. Phys. 14:85–94, "Alternation in Hematopoietic Stem Cell Seeding and Proliferation by Both High and Low Dose Rate Irradiation of Bone Marrow Stromal Cells in Vitro".

Thomason, Donald B. and Booth, Frank W., (1990) Am. J. Physiol. 258, Cell Physiol. 27:C578–C581, "Stable Incorporation of a bacterial gene into adult rat skeletal muscle in vivo".

Kunkel, L. M., (1988) Proc. R. Soc. Lond. B 237:1–9, "Muscular Dystrophy: a Time of Hope".

vanBeek, M. E. A. B. et al., (1986) Radiation Research 108:282–295, "Variation in the Sensitivity of the Mouse Spermatogonial Stem Cell Population to Fission Neutron Irradiation during the Cycle of the Seminiferous Epithelium".

SATELLITE CELL PROLIFERATION IN ADULT SKELETAL MUSCLE

The United States government may own rights in the present invention pursuant to NASA grant NAG2-239 (F.W.B.), PHS grant AB19393 (F.W.B.), and postdoctoral training grant DK07520 (D.B.T.).

The present application is a continuation of U.S. Ser. No. 07/479,065, filed Feb. 12, 1990, now abandoned.

BACKGROUND OF THE INVENTION

1. Field of the Invention

The present invention relates to the field of molecular genetics and its use in the preparation of therapeutic agents effective in vivo in adult tissue. More particularly, stem cells are genetically modified in vivo and then function to induce regeneration and repair of damaged tissue throughout the life span of an animal. More specifically, the present invention relates to the retroviral-mediated transfer of marker genes into adult tissue in which a mitotically-active state of satellite cells has been induced.

Additionally, the present invention relates to methods of treating genetically-transmitted diseases. The invention also relates to methods and therapeutic treatments for regenerating damaged muscle tissue, as a particular method for muscle regeneration in persons with muscular dystrophy is disclosed.

2. Description of Related Art

The insertion of foreign genes or DNA into an organism's genome has become a powerful tool in experimental biology during the past decade. This modification of genetic information has been attempted via the development of a variety of experimental protocols. Many experiments have transferred genes into mammalian cells in culture and into newly fertilized mammalian eggs that then develop into an intact animal. Less commonly, experiments have been performed wherein foreign DNA is inserted into the genome of cells of young or adult animals in situ. The insertion of foreign DNA into the genome of a cell or embryonic tissue has been postulated to be applicable in the treatment of genetic diseases in higher eukaryotes, particularly in humans. Methods currently under extensive study in the manipulation of genes include in vitro DNA transfection techniques, in vivo whole cell injection (i.e., hematopoetic and myoblast cells), and in vivo as well as in vitro retroviral-mediated gene transfer.

The insertion of foreign genes into an organism's genome thus presents a potentially revolutionary method for treating genetic-defect tractable diseases in man. However, many of these genetic diseases remain to be more fully characterized before gene therapy can be used in their treatment.

Some of the more fully characterized examples of genetic-defect diseases identified in the literature include, by way of example, the various forms of muscular dystrophy (see Table 1), diabetes, hemophilia and albinism. The various forms of muscular dystrophic diseases appear below.

TABLE 1

The Progressive Muscular Dystrophies

| Type of Dystrophy | Age of Onset | Pattern of Muscular Involvement | Special Features | CK Level | Inheritance |
|---|---|---|---|---|---|
| Duchenne | Infancy or early childhood | Pelvifemoral; later pectoral girdle | Hypertrophy-pseudohypertrophy; cardiac involvement; mental retardation | High | X-linked recessive |
| Becker | Childhood, adolescence, or early adult | Pelvifemoral, later pectoral girdle | Cardiac involvement, sight; mentation normal | Moderate | X-linked recessive |
| Emery-Dreifuss | Childhood, adolescence | Humeroperoneal | Contractures posterior neck and biceps muscles | Moderate | X-linked recessive |
| Landouzy-Dejerine | Late Childhood, adolescence girdle-late | Facioscapulo-humeral; pelvic normal | Heart normal, mentation | Slight to moderate | Dominant |
| Scapulohumeral of Seitz | Childhood, or adult | Spinal and humeral, later pelvic girdle girdle-late | Cardiomyopathy | Slight to moderate | Dominant |
| Limb-girdle (Erb) | Childhood, adolescence, sometimes adult | Pectoral or pelvic or both | Heart usually normal, mentation normal | Slight to moderate | Variable, recessive, or dominant |
| von Graefe-Fuchs | Childhood, adolescence | Ocular (sparing pupils); later facial and other muscles (slight) | Kearns-Sayre group have retinitis pigmentosa, heart block, stunting of growth, and ovarian dysgenesis | Slight to moderate | Dominant; Kearne-Sayre recessive |
| Oculopharyngeal | Middle or late adult | Levators of lids; other ocular- | | Slight to normal | Dominant |

TABLE 1-continued

The Progressive Muscular Dystrophies

| Type of Dystrophy | Age of Onset | Pattern of Muscular Involvement | Special Features | CK Level | Inheritance |
| --- | --- | --- | --- | --- | --- |
| Myotonic (Steinert) | Infancy, childhood, adult | pharyngeal muscles later Ocular, facial, Sternomastoid, forearm, peroneal | Cataracts, testicular atrophy | Slight to normal | Dominant |
| Congenital | Birth, Infancy | Pectoral and pelvic girdles, or diffuse | Mental retardation, arthrogryposis | Slight to moderate | Dominant or recessive |

Among the many genetic diseases described, the muscle degenerative, or muscular dystrophy-causing diseases, have experienced significant recent technological advances. For example, the muscular dystrophies have been traced to particular gene defects, the elucidation of which has experienced particularly significant scientific breakthroughs in terms of genetic molecular characterization. The most widely known of the muscular dystrophies are Duchenne's muscular dystrophy and the less severe Becker muscular dystrophy. Both of these genetic diseases are characterized by an inability of the muscle to produce dystrophin, which is a muscle protein. This defect is an x-linked recessive disease potentially caused by a defect in the dystrophin gene. The dystrophin gene has most recently been established as having a close relative gene on human chromosome 6[24].

Prior studies have attempted the use of foreign normal myoblast injection as a form of gene product replacement. For example, foreign myoblasts containing a normal dystrophin gene have been injected into dystrophic tissue to invoke the expression of the dystrophin protein in the muscle tissue. However, this method presents the inherent risk of immune rejection, as well as the necessity of injection at multiple, probably closely-spaced sites[23]. Additionally, injection at multiple sites is necessary with such a therapy because dystrophin, like other muscle proteins, tends to remain localized within a single fiber, close to the nuclei from which it was derived. An additional limitation of currently practiced myoblast-injection techniques is the low fusion rate of implanted myoblasts into normal host muscle tissues.

Muscle tissue is characterized by the presence of satellite cells, which are located between the basal lamina and the sarcolemma of the skeletal muscle fibers. Satellite cells in skeletal muscle are dormant stem cells which are present outside the muscle fibers in an adult skeletal muscle. Each of these inactive stem cells can either proliferate into many satellite cells or mature into an embryonic myoblast upon the appropriate stimulation.

By way of example, satellite cells of the muscle have been shown to become stimulated to replicate by muscle damage (Allbrook, 1981; Carlson et al., 1983). It is also possible that strenuous exercise may stimulate cells to become mitotically active and to replicate.[27] Chemical damage via bupivacaine injection into mammalian skeletal muscle cells has been shown to result in rapid recovery of the tissue showing maximum proliferative capacity of satellite cells 36–48 hours following damage[6,14]. As stem cells, satellite cells function to supply myonuclei to growing fibers in immature animals as well as to provide myogenic cells for muscle regeneration and repair throughout the life of the animal.

Several laboratories have published protocols by which the hematopoietic cells of mice have had new genes introduced with retroviral vectors ex vivo, with subsequent reintroduction of the treated cells into the bone marrow in vivo[22]. In this system, marrow cells are obtained from a donor and incubated with a monolayer of vector-generating producer cells. Since marrow cells, unlike the producer cells, do not attach to the culture disk, they are easily recovered after co-cultivation. The hematopoietic cells are then introduced into a recipient animal by intravenous injection. Space in the hematopoietic system to receive the vector-treated marrow must be made usually by lethally irradiating the recipient. While this technique has been widely used experimentally, its use in humans is limited by the recurrent risk of host immune rejection, as current studies on muscle were performed on mdx (immunosuppressed) animals[23]. Additionally, low proportion of cells incorporate the normal myoblast dystrophin gene in myoblast transfer procedures. Moreover, multiple injections of myoblasts are typically required to achieve proper dispersion of the myoblasts in situ.

A need thus remains in the art for the development of a therapeutic system which minimizes or eliminates host immune response, perhaps through the development of an entirely in vivo vector-induced, host cell gene incorporation process. However, technical difficulties in the manipulation of genomes from organisms both in achieving the initial incorporation of the desired gene by the host cells as well known as achieving expression of those genes in the host have limited techniques of direct incorporation of a gene without a "carrier" cell into damaged tissue in vivo. DNA transfection and retroviral mediated gene incorporation are two methods of such a "direct gene" incorporation which eliminates the need for a "carrier" cell.

The treatment of genetically-related diseases with techniques as DNA transfection has thus far, unfortunately, not met with great success. In DNA transfection, DNA (presumably which includes a non-defective counterpart of the defective gene) is introduced into cells in culture as part of a coprecipitate with calcium phosphate or dextran sulfate.[9] A successful result is a viable cell containing one to many copies of the new gene which continuously expresses the new genetic information.

While several limitations exist in this system, the most significant limitation is that it is a very inefficient means of transferring genes into mammalian cells. For example, only one in a thousand cells (more typically, one cell in a million) will incorporate the newly transformed gene. Additionally, not all cultured cell lines are susceptible to this method of gene transfer. For example, while the stem cells located in bone marrow are typically susceptible to this method of gene transfer, they are present only as a small fraction (less than one cell in a thousand) of the total nucleated cells of the tissue. Another limitation is that it is an ex vivo technique.

This method is therefore inefficient as only a small population of cells incorporate the desired gene, failing to accomplish gene delivery to a large fraction of a target cell population. Even if the technical difficulties of gene incorporation overcome, a second obstacle to the effective employment of this technique in the higher eukaryotes and mammals which has not yet been solved in being able to attain proper expression of successfully incorporated genes by the host.

Retroviral-mediated gene transfer (i.e., the use of retroviruses to deliver genes into cells) is an alternative gene transfer technology which has met with a limited, yet improved, success in host genome incorporation rates. Using this technique, it is now possible to insert a gene into a retroviral vector to obtain a recombinant virus, and then infect target cells with the retrovirus (which includes a particular gene of interest) and achieve the expression of the foreign gene by the host cell's chromosomes. Retroviruses are RNA viruses, that is, the viral genes are encoded in an RNA molecule rather than in a DNA molecule. All RNA tumor viruses are members of the retrovirus family, but not all retroviruses are oncogenic or even pathogenic.

In retroviral-mediated gene transfer, the viral RNA is first converted to DNA when an RNA virus penetrates a cell. If the cell penetrated is a replicating cell (i.e. mitotically active), the DNA will enter the nucleus and integrate into a chromosome. This integrated DNA becomes indistinguishable as far as the cell is concerned from any other cellular gene. It is from this integrated form, that the viral genes are expressed. In this process, integration of the viral genome into the cell's chromosome is an essential part of its replication. However, RNA retroviruses only insert their genome into mitotically active cells; thus making it highly unlikely that an RNA retrovirus would infect a mature myonucleus. Thus, only immature animal tissues have been used experimentally with retroviral-mediated gene transfer systems with much improvement of gene-incorporation rates.

Retroviral mediated gene transfer remains a relatively inefficient gene transfer system for adult tissues owing to low gene incorporation rates of target cells. It would therefore only be by means of a highly efficient retroviral vector system that genetic manipulation of totipotent stem cells would become practical, as currently practiced methods of retroviral-gene transfer provide only a small fraction of genetically-altered cell components.

A number of procedures are known to artificially induce a mitotically-active state in a cell population. For example, exercise,[27] tissue trauma,[6] chemical injection,[28] and radiation[9,30] have been shown to make tissue or cells in culture mitotically active. Many pharmaceutical agents (especially anesthetics, such as Marcaine®) have been found to destroy or damage muscle fibers.[28] For example, it has been found that when bupivacaine (a local anesthetic) is injected into skeletal muscle, existing muscle fibers (including myonuclei) are destroyed,[15,16] curiously, however, the satellite cells in these tissues are left undamaged.

Despite developments in retroviral-mediated gene transfer and studies regarding the in vitro and in vivo induction of mitotically active states in certain cell populations, the many unknown aspects of the structure and function of retroviruses have prevented the combination of these advantages in the development of an efficient gene-transfer system. Technical difficulties still exist in the use of retroviral vectors for gene transfer in large animals (i.e., humans), such as in the efficiency of infection of pluripotent stem cells and in the long-term stability of expressed genes. Moreover, the use of retroviral-mediated gene transfer is limited by the size of the gene constructs which the virus is able to carry. For example, genes having more than 1400 base pairs have been found to be too large for common vectors. Such results in difficulties in replacing proteins, either for functional studies or in gene therapy experiments, which involve genes of this size.

In the development of an efficient retroviral gene transfer system, two parameters must be optimized. First is the capacity to infect a large proportion of the target cells, a property dependent at least in part on the ability to generate a high concentration (or titer) of recombinant virus. Second is the capacity to have the gene expressed properly in the host.

An intense need exists in the art of molecular biology to either circumvent the limitations of retroviral-mediated gene transfer (gene size, gene incorporation ratio in target cells) if retroviral vectors are to be used in the medical treatment of genetic disease in humans. Additionally, the need for an efficient gene transfer system is desirable for its usefulness to basic research, as well as being an absolute prerequisite for application to human therapy.[10]

The innovative development of gene transfer technology to improve target cell incorporation ratio while achieving successful and acceptable amounts of gene expression in the host, while eliminating host immune-response problems, would revolutionize currently practiced methods of treating genetically-induced maladies, especially those muscle degenerative diseases which have escaped human intervention over the years.

SUMMARY OF THE INVENTION

The present invention presents a surprisingly effective and novel in vivo method of expressing foreign genes in an adult eukaryotic tissue. This method accomplishes the incorporation of a foreign gene of interest using a retroviral-mediated gene transfer system wherein the target tissue is first treated so as to induce a mitotically-active state in the cells of the target tissue.

The present inventive method also presents an amazingly accurate and simple technique applicable to the study of eukaryotic tissue regeneration, especially the regeneration of muscle tissue. For example, with the presently disclosed innovative retroviral gene transfer system, Applicants have been able to reveal for the first time two important aspects of the cell biology of the muscle. First, that in damaged muscle, a satellite cell directs its daughter myoblasts almost exclusively to a single regenerating fiber. Second, Applicants' studies show that the apparent diffusion domain of a myonucleus overlaps several adjoining myonuclei, confirming the possibility of internuclear communication of factors that may regulate gene expression in tissue, particularly that in muscle tissue.

In its broadest embodiment, the present invention comprises a method for the in vivo incorporation of a foreign gene into an adult tissue comprising infecting a mitotically-active cell in the living tissue with a retroviral vector. The retroviral vector of the present invention most preferably comprises a replication deficient retrovirus and a foreign gene. In one preferred embodiment of the claimed method, the foreign gene of the retroviral vector is a prokaryotic foreign gene. This prokaryotic foreign gene is in one application of the invention, the β-galactosidase gene of E. coli.

In still another embodiment of the claimed method, the foreign gene of the retroviral vector is a eukaryotic gene. Most preferably, when the foreign gene is a eukaryotic foreign gene, the gene is a gene encoding dystrophin protein, or dystrophin gene, or a gene encoding insulin, or an insulin gene. Of these, the eukaryotic dystrophin gene is most preferred. The dystrophin gene is in a modified form as a dystrophin gene construct, which is significantly smaller than the naturally occurring dystrophin gene. Such is provided in order to allow the containment of the dystrophin gene construct in a single retroviral vector.

In that the present methods allow for the incorporation of a single gene in a living tissue, particularly muscle tissue, the present invention allows for the follow-up study of the effect of the in vivo specifically-altered genome on tissue function resultant from the incorporation of a particular foreign gene. Additionally, the study of the control of gene expression in tissues so genetically altered is also facilitated.

Foreign gene expression in intact adult animals is achieved with the present invention through the efficient incorporation of the foreign gene into the genome of the target tissue or cells thereof. For this purpose, a retrovirus which is replication deficient is employed, which includes a gene encoding a desired gene product. In that the present invention encompasses a method of gene incorporation, a method of gene therapy for the replacement of a defective or deficient gene is also disclosed. The gene which is to be incorporated by the target cells in this method encodes a product which supplies or is complementary to a particular genetic deficiency present in the animal.

An object of the present invention is to eliminate the problem of immune response attendant many forms of gene transfer. Applicants' method of incorporating a single foreign gene into eukaryotic cells completely in vivo, employing only a retroviral vector, effectively eliminates the risk associated with immune rejection inherent to other techniques involving whole cell (e.g., myoblast) injection.

The presently disclosed methods accomplish genetic complementation and repair totally in vivo, as compared to other techniques which require ex vivo vector transformation of donor or recipient cells prior to treatment of the diseased or damaged tissue (i.e., donor myoblast retroviral infection and recipient injection of transformed myoblasts). Pursuant thereto, the present invention features the advantage over prior methods of avoiding host immune rejection of vector-transformed cells. While this obstacle does not exist when host autologous cells are used as the vehicle of gene transformation, sufficient host autologous cells may not be available for genetic therapy prior to their reintroduction into the host. Limitations of the system attendant the availability of a sufficient population of the host cells (as the transforming agent) are eliminated by doing away with the need for extraction and genetic manipulation of the transforming cells. The risk of potential damage from manipulation of the transforming agent (i.e. host cells) is also eliminated.

A preferred embodiment of the presently described method for incorporating a foreign gene into an adult eukaryotic tissue completely in vivo comprises: inducing a mitotically-active state in an adult eukaryotic tissue to produce mitotically active eukaryotic cells; preparing a retroviral vector comprising a gene of interest; and exposing the mitotically-active cells to the retroviral vector for a time period sufficient to allow genetic incorporation of the gene of interest in the genome of the mitotically-active cells of the eukaryotic tissue. Most preferably, the retroviral vector is replication deficient, and the gene of interest comprises a gene encoding an enzyme or protein which is complementary to the deficiency or supplies the product of a defective gene in the host tissue being treated.

The gene of interest in one particularly preferred embodiment of the described method comprises a prokaryotic foreign gene. In such a preferred embodiment, the prokaryotic foreign gene is a β-galactosidase gene. The gene of interest in still another particularly preferred embodiment of the described method is a eukaryotic foreign gene. Preferred embodiments of the disclosed methods which include a eukaryotic foreign gene are further defined as comprising a eukaryotic gene such as an insulin gene, a dystrophin gene or a spectrin gene, or phenotypically sufficient fragments or constructs thereof. Thus, in one particularly preferred embodiment, the gene of interest is a dystrophin eukaryotic gene construct which is a modified dystrophin gene having between 7,000–10,000 base pairs.

In that the present methods may employ any eukaryotic gene of interest in the retroviral vector, the described methods also comprise a method of gene therapy. As a method of gene therapy, a particular defective gene in a eukaryotic tissue is replaced or substituted in vivo by a complementary non-defective gene in the cells of the eukaryotic tissue. In such an embodiment, the present method of gene therapy for the replacement of a defective gene in a eukaryotic tissue comprises: inducing a mitotically-active state in the eukaryotic tissue to produce mitotically-active cells; preparing a retroviral vector comprising a gene complementary to the defective gene in the eukaryotic tissue; and exposing the mitotically-active cells to the retroviral vector for a time period sufficient to allow the incorporation of the gene of interest in the eukaryotic cell, wherein incorporation of the gene of interest replaces the defective gene in the cells of the eukaryotic tissue. In a most preferred embodiment of this method, the gene complementary to the defective gene is a eukaryotic gene, such as the dystrophin gene for the treatment of animals with degenerative muscle disease.

As a method for treating a genetic disease in a eukaryote, the invention comprises incorporating a complementary gene to a genetic deficiency in a stem cell of the eukaryote, wherein incorporation of the complementary gene comprises the steps of: inducing a mitotically-active state in the cells of the eukaryote to form a mitotically-active preparation of eukaryotic stem cells; preparing a retroviral vector comprising a eukaryotic gene complementary to the genetic deficiency in the cells of the eukaryote; exposing the mitotically-active preparation of eukaryotic stem cells to the retroviral vector; and incubating the retroviral vector with the mitotically-active preparation of eukaryotic cells a time period sufficient to allow incorporation of the complementary gene in the eukaryotic stem cell. In this manner, the deficiency in the eukaryotic genome is eliminated.

Most preferably, the eukaryotic cell described in the present methods include totipotent eukaryotic cells, such as a stem cell (i.e., muscle satellite cells, hematopoietic stem cells (in bone marrow)[13], dark basal keratinocytes[31]). As used in the present application, the term "totipotent" relates to a cell which is capable of differentiating into an entire organism or into a part of an organism, such as a cell which is capable of generating or differentiating to form a particular tissue (i.e., muscle, skin, heart, brain, uterus, testis, blood).

The eukaryote described in the present invention includes all organisms comprising cells which contain a membrane-bound nucleus. In particularly preferred embodiments of the described methods, the eukaryotic tissue described in relation to the disclosed methods is human tissue, rat tissue or mouse tissue.

In the more preferred embodiments of the described methods, a mitotically-active state in a living eukaryotic cell or tissue comprises inducing cellular-repair mechanisms in the cell or tissue. Thus, the induction of a mitotically-active state comprises discomposing the tissue, exposing the cell to radiation, or administering a pharmaceutical chemical agent. As used in this application, the term discompose relates to any change in the normal resting state or non-mitotically active state of a eukaryotic cell culture or tissue, particularly that of a eukaryotic tissue. By way of example, discomposition of a tissue may be accomplished through vigorous exercise stimulation[7], agitation, surgical intrusion or other trauma of the tissue or cell culture.

The use of chemicals to induce a mitotically-active state in the cell (i.e., in cell culture) or tissue described includes the administration of any of a variety of pharmaceutical agents. By way of example, the pharmaceutical agents capable of inducing a mitotically-active state in vitro or in vivo include bupivacaine, collagenase, dexamethasone, fibroblast growth factor, and any other reagent capable of inducing a mitotically-active state in a eukaryotic tissue or a eukaryotic cell.

The retroviral vector is a retrovirus (RNA virus) which is replication deficient or replication incompetent. That is to say, the retrovirus lacks one or more of the replication genes, gag (group-specific antigen), pol (polymerase) or env (envelope) protein encoding genes.

The gene therapy of the present invention comprises a method by which any of a variety of genetic diseases may be eliminated. The invention thus comprises a method of treating genetic disease. Such is accomplished through the successful incorporation of a particular complementary gene or part of a complimentary gene in the genome of totipotent cells of the diseased organism, thereby facilitating the production of cells in the diseased host with similarly corrected genomes. By way of example, genetic diseases which may be treated employing the described methods include diabetes, albinism, and the various forms of muscular dystrophy. However, any recessive gene is hypothesized to be treatable employing the described methods of gene transfer and gene replacement.

In a most preferred embodiment, a method for treating the genetic disease of muscular dystrophy is described. Muscular dystrophy is a genetic disease characterized by a defective gene encoding the muscle protein, dystrophin. In this particular embodiment of the invention, the gene of interest would be a part of the dystrophin gene (i.e., a dystrophin gene construct) which encodes a part, segment or fragment of the dystrophin protein, this particular protein segment supplying a sufficient part of the native dystrophin protein to protect the eukaryotic tissue from all but only the mildest phenotypic manifestation of muscle degeneration. This particular dystrophin gene fragment is described by England et al.[20]

The spectrin gene, which encodes a muscle protein similar to dystrophin, is also hypothesized to be effective in the methods described herein for the treatment of muscular dystrophy. More particularly, a retroviral vector which includes a spectrin gene or a fragment of the spectrin gene may be effective in treating muscular dystrophy through the injection of such a retroviral vector into a eukaryotic tissue, the eukaryotic tissue being treated so as to induce a mitotically active state therein. Various methods for inducing such a mitotically active state are as otherwise described herein (radiation, trauma, exercise, chemical injection).

The retroviral vector in one preferred embodiment of the present invention would include a dystrophin gene construct which encodes a particular dystrophin protein fragment which is effective to halt massive or significant muscle degeneration, as well as to regenerate already damaged muscle tissue. In a most preferred embodiment of the invention for the treatment of muscular dystrophy, the retroviral vector includes a dystrophin gene construct comprising between 7,000–10,000 base pairs. In an even more preferred embodiment, the dystrophin gene construct comprises about 9,000 base pairs of the native dystrophic gene. This dystrophin gene construct encodes a protein having a relative molecular weight of about 200,000 K.

As a method of treating muscular dystrophy in a human or other eukaryotic organism, the present invention in a most preferred embodiment comprises the initial induction of a mitotically-active state in the tissue of the eukaryote through the intramuscular administration of bupivacaine to the skeletal muscle tissue. The retroviral vector of this particular embodiment of the invention comprises a replication defective murine leukemia virus. Most preferably, the murine leukemia virus comprises AKR, Moloney or Friend leukemia virus. However, most preferably, the retroviral vector comprises the replication defective Moloney murine leukemia virus.

In still another embodiment of the present invention, the retroviral vector comprises a prokaryotic gene, such as a β-galactosidase gene, wherein the β-galactosidase gene is under the control of the retroviral 5' long terminal repeat promoter region. More particularly, the β-galactosidase gene is under the control of a constitutive promoter[3]. A method for monitoring gene expression in tissue is thereby provided (i.e., focal and diffuse expression). For example, as employed to infect muscle tissue in eukaryotes, Applicants propose that the use of such a vector system would track regenerating and fully recovered muscle fibers, in that regenerating and fully recovered muscle fibers would express the β-galactosidase gene product if the infected satellite cells gave rise to viable myoblasts.

The disclosed methods are not to be limited to treatment of muscular degenerative diseases. For example, the gene of interest in the present invention may comprise any gene or part of any gene which complements a deficiency in the animal being treated. However, length of the gene of interest, or the coding region thereof, is preferably less than 14,000 base pairs so as to facilitate the inclusion of the particular gene in a single retrovirus.

Use of the presently described methods to stimulate stem cell proliferation allows the transformation of the genome of, in one particular embodiment, skeletal muscle satellite cells, resulting in the production of genetically-corrected myoblasts. These myoblasts then become the non-defective myonuclei of newly formed and non-defective muscle fibers. As will be appreciated, the invention in such an application comprises a method for regenerating muscle tissue. In a most preferred embodiment, this technique comprises a method of treating degenerated dystrophic muscle tissue. In this preferred embodiment, the regeneration of dystrophic muscular tissue, characteristic of such diseases as Duchenne's muscular dystrophy and Becker muscular dystrophy, is specifically envisioned.

As a therapeutic treatment for muscular dystrophy, Applicants have found that the technique of stimulating stem cell proliferation to allow retroviral-mediated gene transfer is generally applicable to all eukaryotic tissues. Potential target cell populations for use with the present methods are characterized by the presence of stem cells. By way of example, tissues expected to be susceptible to the described treatments and methods are those tissues which include stem cells. By way of example, these stem-cell containing tissues include those tissues of the uterus, skeletal muscle, liver, kidney, blood, alimentary epithelium, testes, skin and gastrointestinal tissue. The stem cells of muscle tissue are the satellite cells. In the described methods, the stem cells (i.e., satellite cells) in muscle tissue are the cells which are infected with the retroviral vector to facilitate incorporation of the eukaryotic gene of interest in the satellite cell itself. These satellite cells may then function to supply myonuclei to growing fibers in immature animals and to provide myogenic cells for muscle regeneration and repair throughout the life of an animal.

In that any of the methods described in the present application may be used in vivo, the retroviral vector may be further defined as comprising a retroviral vector conjugated to a protein. Such may be accomplished by methods well known to those of skill in the art, and will function to enhance the targeting of the vector to particular populations of target cells.

The following abbreviations are used throughout the Specification:

CFU=colony forming units
ug=microgram
EGTA=methylene glycol tetraacetic acid
β=beta
um=micromolar
β-galactosidase=beta-galactosidase (EC 3.2.1.23)
MoLV=Moloney murine leukemia virus

DETAILED DESCRIPTION OF PREFERRED EMBODIMENTS

Figure 1A:
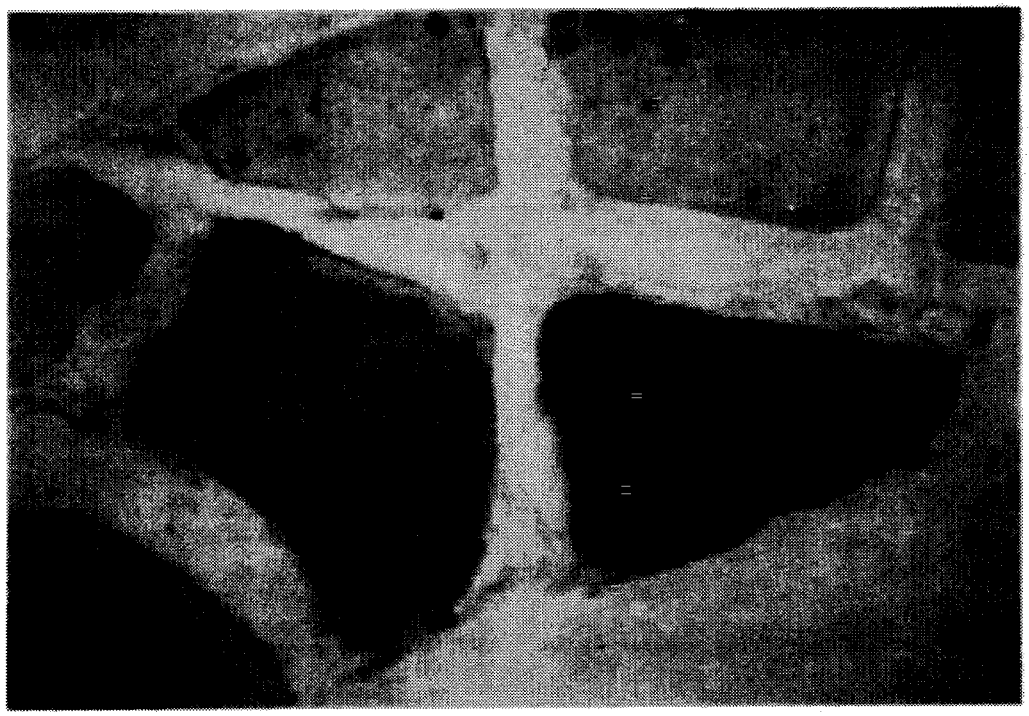
FIG. 1—β-galactosidase expression in soleus muscle sections. 24–48 hours after muscle damage the bupivacaine-damaged muscle and undamaged contralateral muscle were injected with 0.3 ml of the retrovirus carrying the β-galactosidase gene ($2\times10^5$ CFU/ml). The animals were then housed in a biohazard facility for one week or four weeks. 16 um frozen sections were stained for β-galactosidase activity using the method of Dannenberg and Suga[8] to produce a distinct indigo blue precipitate. (A) Cross-section. Diffuse β-galactosidase activity occurs within the circumference of the fibers with adjacent fibers occasionally exhibiting less intense staining. (B) Cross-section. More focal staining is often observed associated with the sarcolemma. (C) Longitudinal section. Diffuse β-galactosidase activity occurs uniformly over many nuclear domains. (D) Longitudinal section. Focal activity along the length of a fiber. The magnifications in all panels are identical; the length bar in (D) represents 10 um.

The inventions of the present disclosure relate generally to gene transfer systems in eukaryotic cells and tissues. The practice of the invention provides an improved transfer system for eukaryotic and prokaryotic genes surprisingly improved over other practiced gene-transfer systems. For example, improvements of the present system include an enhanced gene incorporation rate in a target cell population, successful target cell expression of the host-incorporated foreign gene, and elimination of host-immune rejection response. These methods of gene transfer are effected through the induction of a mitotically-active state in a target cell population prior to exposure to a retroviral vector. Target cells thus become receptive to retroviral gene insertion, thus greatly enhancing the rate of gene incorporation. Use of the direct in vivo injection of a retroviral vector eliminates the risk of host-immune response existent in 37 carrier cell" type gene transfer systems (i.e., in vitro myoblast modification and subsequent in vivo injection).

It is desirable that the retrovirus employed be replication deficient and be a murine leukemia virus. In most preferred embodiments of the invention, the retrovirus is an AKR, Moloney or Friend murine leukemia virus. Moreover, it is particularly desirable that the retrovirus include a particular gene of interest which is complementary to or provides a suitable substitute for a defective or deficient gene in the target cell population or tissue.

In a most preferred use of the described invention, a method for the in vivo incorporation of a foreign gene into an adult tissue is described comprising infecting a mitotically-active cell in the adult tissue with a retroviral vector. The retroviral vector in such a preferred embodiment comprises a eukaryotic foreign gene and is replication defective.

As a method of gene therapy, the present invention discloses a technique whereby a defective gene in a eukaryotic tissue may be replaced. This particular method comprises inducing a mitotically-active state in the eukaryotic tissue to produce mitotically-active cells; preparing a retroviral vector comprising a eukaryotic gene complementary to the defective gene in the eukaryotic tissue; and exposing the mitotically-active cells to the retroviral vector for a time period sufficient to allow incorporation of the gene of interest in the eukaryotic cell. By this method, the incorporation of the gene of interest functions to replace the defective gene in the eukaryotic tissue.

The present invention presents a revolutionary method for treating virtually any disease caused by a genetic deficiency in a eukaryote. Such is accomplished through the incorporation of a non-defective gene complementary to the particular deficiency in the diseased organism. More particularly, the incorporation of a particular complementary gene comprises a series of steps, wherein a mitotically-active state is first induced in the eukaryote cells, most preferably stem cells of the eukaryote. Thus, the general scheme of the technique, i.e., stimulating stem cell proliferation followed by retrovirus injection is postulated to provide a means to facilitate gene transfer into many different tissues.

Applicants' studies demonstrate the described foreign gene incorporation into mammalian adult skeletal muscle. Accordingly, from these studies, it is hypothesized similar gene incorporation may be accomplished in smooth muscle, gastrointestinal, brain, cardiac muscle, uterine, blood, skin or testicular tissue, especially those tissues as they exist in the human.

Turning now to a consideration of the methods by which a mitotically-active state may be induced in a viable adult eukaryotic tissue or a eukaryotic cell culture, such a receptive state may be induced via any discomposition which induces cellular-repair mechanisms in a cell culture or tissue. As will be recalled, retroviruses are unable to insert genetic information into another cell unless that target cell is made receptive (i.e., mitotically active). A receptive state of a target cell may be induced by making the cell mitotically active. A variety of techniques are available which induce such a mitotically-active state. By way of specific example, such includes the irradiation of the tissue or cell culture, the exposure of the cells or tissue to particular pharmaceutical agents, the physical agitation of a cell culture, or the surgical intrusion of a tissue, as well as through the vigorous exercise of a tissue.

Among those pharmaceutical agents expected to be effective in inducing the described mitotic or active state in cell culture or in vivo, the following list presents those agents most particularly preferred: collagenase, fibroblast growth factor, bupivacaine, estrogen and dexamethasone.

The following tissue sectioning and staining protocol represents a method which may generally be used in the fixation of any type of tissue from any of a variety of animal species. Several experimental examples follow thereafter which are designed to illustrate particularly preferred embodiments of the inventions, both as they actually exist and as they are proposed to exist in the future (i.e., prophetic exemplary use in treating genetic disease in humans).

It should be appreciated that many modifications and changes can be made in the particular stimulatory agents and their doses, the particular retroviral construct (i.e., the promoter, the gene of interest, and the particular retrovirus) and the particular conditions under which the retrovirus introduced to a culture of cells or into a living adult tissue without departing from the spirit and scope of the invention.

Tissue Sectioning and Staining

Muscle sections were stained by the method of Dannenberg and Suga.[8] Briefly, 16 um sections were mounted on 0.5% gelatin slides and fixed 5–10 minutes at 4° C. with the same fixative as used in the dissection. The sections were washed briefly with PBS containing 2 mM $MgCl_2$ at 4° C. and once again for 10 minutes with the same solution. The sections were then washed for 10 minutes in PBS containing 2 mM $MgCl_2$, 0.01% sodium deoxycholate, and 0.02% Nonidet P40 at 4° C. The slides were briefly dried and stained for 18 hours at 37° C. in a PBS solution containing 35 mM $K_3Fe(CN)_6$, 35 mM $K_4Fe(CN)_6 \cdot 3H_2O$, 2 mM $MgCl_2$, 0.01% sodium deoxycholate, 0.02% Nonidet P4, and 1 mg/ml 5-bromo-4-chloro-3-indoyl-b-D-galactopyranoside (Xgal). Following staining the slides were rinsed three times for 5 minutes each with PBS at room temperature, blotted dry, and stained with 5% eosin.

Applicants are in the process of replacing the β-galactosidase gene with the rat insulin-like growth factor I coding region, using the following strategy. The entire β-galactosidase gene was removed from the gag region of the retroviral "BAG" construct of Price, et al.,[3] by restriction with Pvu I and BamHI. The insulin-like growth factor I coding region will be added to the gag site where β-galactosidase was removed as follows. Applicants were supplied with prIGF-Ib-42-a, a 422 bp insert in pUC-19, which included a partial 5' untranslated region with 2 putative ATG translation start sites, the Pre, B, C, A, D and part of the E domains of the rat insulin like growth factor 1 coding region, without introns. The processed mature insulin-like growth factor I peptide did not contain the E domain. The 422-bp insulin-like growth factor I coding region was flanked by EcoRI restriction sites.

BL-2 tissue culture facility

An 80 $ft^2$ room was devoted solely to culture of the Psi2 packing cell line and 3T3 cells, which were used to prove that the produced retrovirus is replication-incompetent, that is no recombinant wild-type retrovirus is produced. A BL-2 rated laminar flow hood (Nuaire 425–400) and a $CO_2$ $H_2O$—jacketed incubator (Nuaire) was also used in the following studies. An Olympus CK2 inverted scope with phase contrast was available outside the culture facility.

Laboratory facilities

Two cryostats (IEC minotome) were available for production of tissue sections. An automatic microtome knife sharpener was also available for usage. Applicants' laboratory has an Olympus BH-2 microscope with attached mOS color video camera so that a slide may be viewed simultaneously through the binocular observation tube and on a video color monitor. This system is attached to a PC Vision Plus Frame Grabber Board in an AT-clone computer. Applicants have a JAVA image-processing program which permits the determination of relative area of indigo blue on a tissue section.

Applicants' laboratory also contains apparatus for electrophoresis of agarose, sequencing and polyacrylamide gels, power supplies, microfuges, water baths, tissue homogenizers, vacuum oven, sterilizer, freezers, gel dryers, pH meters, stirrers, IEC-5000 centrifuge, DNA sequencing apparatus, Geiger counters, recorders, pumps and electrical stimulators. Applicants have access to Departmental low and high centrifuges (Sorvall RC series to Beckman L5-50), gamma and beta scintillation counters, and Gilford spectrophotometer.

EXAMPLES

The following examples further illustrate certain features of particularly preferred methods as provided by the present invention.

Example 1—Preparation of a Retroviral Construct

The replication-defective retroviral construct is that of Price et al[3] Psi2 cells producing the retrovirus containing the β-galactosidase and neomycin phosphotransferase genes (American Type Culture Collection CRL 9560) were grown to confluence in Dulbecos Modified Eagles Medium containing 10% fetal calf serum. The E. coli β-galactosidase gene used was under the promoter control of the retroviral Moloney murine leukemia virus 5' long-terminal repeat promoter region, and thus is constitutively expressed. The medium was withdrawn and replaced with fresh medium. Following three days of incubation, the retrovirus-containing medium was collected, filtered through 0.45 um filters, brought to 8 ug/ml polybrene, and stored at −80° C. A titer of $2 \times 10^5$ colony forming units (CFU) per milliliter was obtained, as determined by infection of NIH 3T3 cells.

The retrovirus was tested for wild-type (replication-competent) viral particles by testing the ability of the conditioned media from infected NIH 3T3 cultures to produce a secondary infection in uninfected cells. No wild-type viral particles were detected, but as a precaution the retrovirus was handled in type IIB culture facilities.

The retroviral construct was used in the experiments described in Examples 2 and 3.

Example 2—In Vivo Foreign Gene Incorporation and Expression in Adult Female Rat Muscle The following experiment was designed to determine if a foreign gene could be successfully inserted and achieve expression in the tissue of a living animal employing a totally in vivo system. The experiment tests a method for inserting a vector which includes a foreign gene, in this case, the E. coli gene coding for β-galactosidase, into the existing DNA of skeletal muscle in adult rats. This system constitutes an effective marker system to follow the incorporation of a gene of interest into a tissue.

To maximize the probability of retroviral gene insertion, the retrovirus containing E. coli β-galactosidase gene was injected into the bupivacaine-damaged soleus muscle of the rat 24–48 hours following damage.

In order to produce bupivacaine damage, the soleus muscles of 125 g female rats were exposed by lateral incisions. The left soleus muscle was injected bilaterally in each quarter with 0.3–0.5 ml 0.5% bupivacaine HCl, 0.1% methylparaben in isotonic NaCl (0.5% Marcaine®, Winthrop-Breon Labs) using a 27 g needle. There was considerable leakage of the liquid from the injection sites. The right soleus muscle served as the contralateral control and was similarly injected with 0.9% NaCl, 0.9% benzyl alcohol (bacteriostatic NaCl). 24–48 hours following bupivacaine damage, both left and right soleus muscles were again exposed and 0.3 ml of the retrovirus-containing medium was administered by injection in the same pattern as the bupivacaine and saline injections. The animals were then allowed to recover either 6 days or one month in a biohazard suite.

Upon dissection, the soleus muscles were placed in a fresh solution of ice-cold 2% paraformaldehyde, 100 mM PIPES, 2 mM $MgCl_2$, 1.25 mM EGTA, pH 6.9, for 15 min. The tissue was then placed in an ice-cold PBS solution containing 2 mM $MgCl_2$ and 30% sucrose for 3 hours. The muscles were blotted dry and embedded in OCT medium (Miles Laboratories) on dry ice. Embedded muscle was stored at −20° C.

The contralateral soleus muscle received saline injections instead of bupivacaine, but otherwise was treated identically to the bupivacaine-damaged muscle.

Figure 1B:
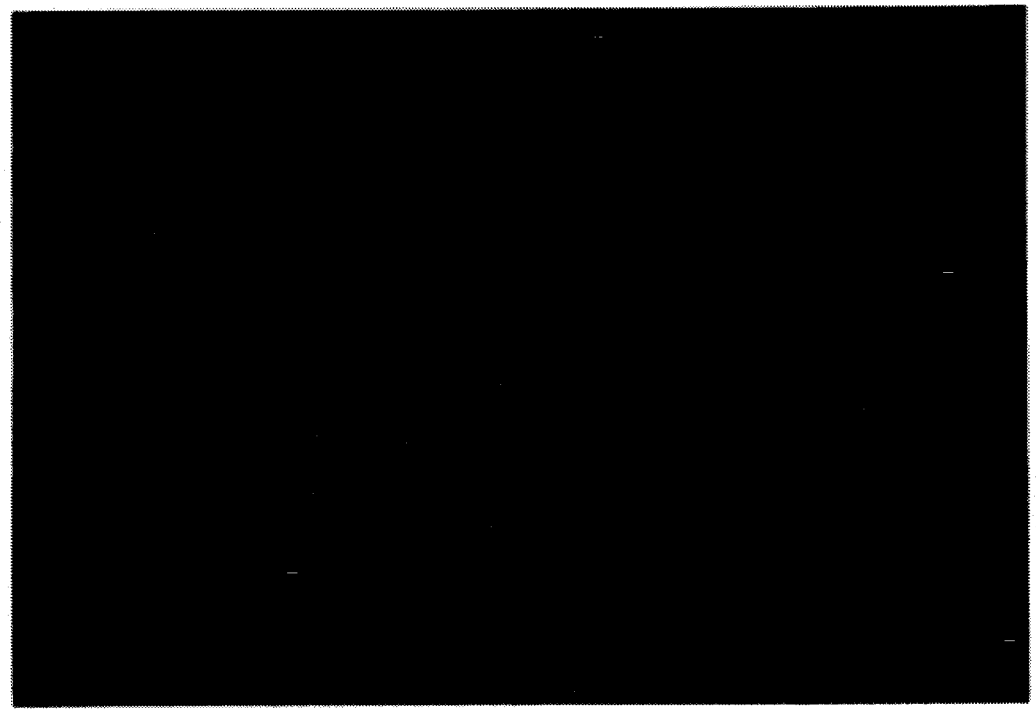
Figure 1C:
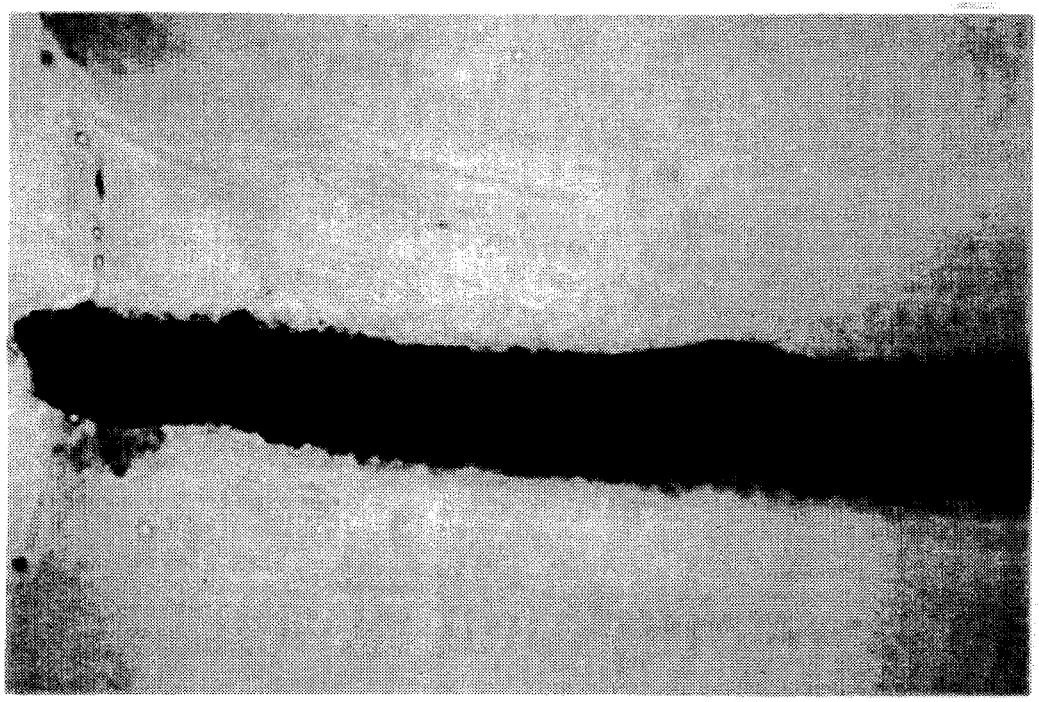
Figure 1D:
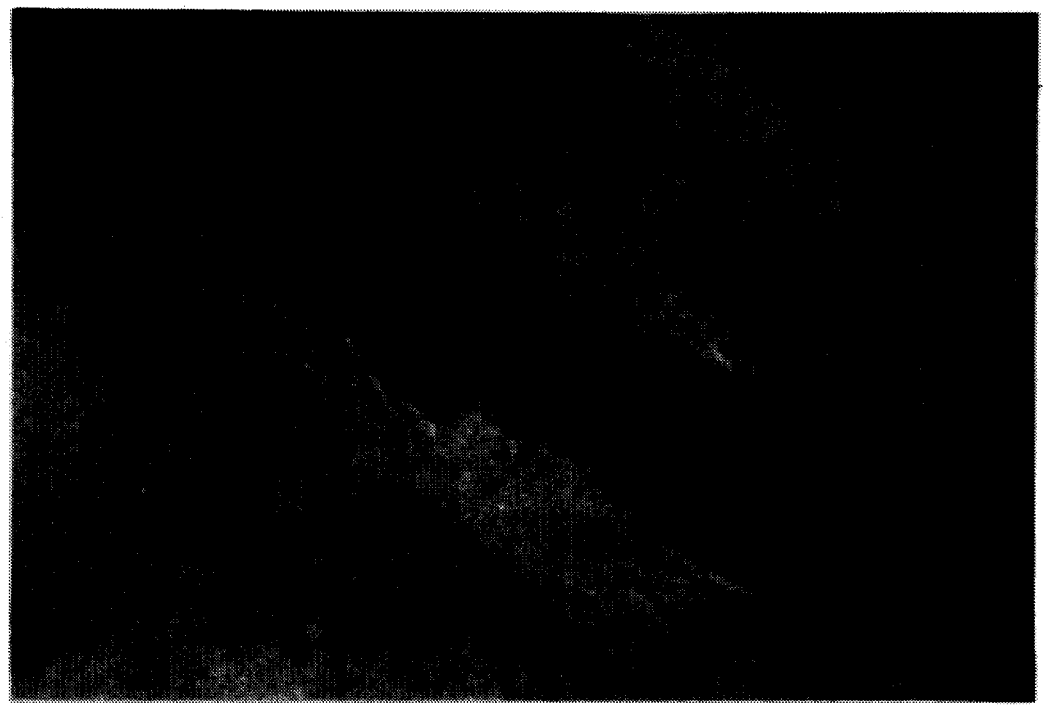

In all cases, injection of the retrovirus into the damaged soleus muscle resulted in the expression of histochemically detectable β-galactosidase activity in satellite cells and muscle fibers within the week following injection (FIG. 1). Furthermore, the expression was stable for at least one month following the injection of the retrovirus. Several tens of fibers were routinely found to express β-galactosidase activity in serial sections, though only a few fibers expressed the enzyme activity densely throughout the entire circumference of the fiber. In contrast, the contralateral control soleus muscle (which received saline instead of bupivacaine injections and was also injected with retrovirus) exhibited far less expression of β-galactosidase activity. (Table 1). Bupivacaine-damaged muscle that did not receive injections of retrovirus did not express β-galactosidase activity.

Diffuse and Focal Foreign Gene Expression In Vivo

Two patterns of β-galactosidase expression, diffuse and focal, were evident. Diffuse expression occurred within the circumference of a single fiber (FIG. 1, A and C). Often an adjacent fiber has a less dense expression of β-galactosidase activity within the fiber circumference; this apparent exclusivity of lineage was not a result of undamaged neighboring fibers because the phenomenon also occurred when the neighboring fibers were regenerating myotubes. Focal β-galactosidase activity occurred immediately adjacent to the sarcolemma (FIG. 1 B and D) and occasionally in the intracellular matrix between fibers. Because this focal expression was maintained even after 1 month of regeneration, the structures associated with this expression might have been satellite cells or their daughter myonuclei. However, because the apparent diffusible domain of a myonucleus overlapped several adjoining myonuclei, Applicants did not expect the expression of the β-galactosidase to be limited to within the myonuclear envelope. Nonetheless, at the present time Applicants do not have an explanation for the mechanism underlying the specific patterns and variability of β-galactosidase expression in the regenerating skeletal muscle, and further do not wish to be limited to any such theory of gene expression in the presently described invention.

Applicants outlined a method to incorporate a single foreign gene into mammalian adult skeletal muscle that does not risk the possibility of immune rejection inherent in techniques involving the injection of infected myoblasts into an animal.[22] The technique introduced here opens the future possibility for the introduction of muscle-specific genes into muscle in vivo, followed by studies of altered muscle function and the control of muscle gene expression.

The general scheme of the technique, i.e., stimulating stem cell proliferation followed by retrovirus injection, may provide a means to facilitate gene transfer into tissues other than muscle tissue. By way of example and not limitation, it is envisioned that the present retroviral mediated gene transfer system would be effective in such tissues as brain, intestinal tissue, cardiac tissue, skin, blood, testicular tissue and uterine tissue.

TABLE 2

| | β-galactosidase Expression | |
|---|---|---|
| | bupivacaine-damaged | control |
| no. of muscles | 8 | 5 |
| no. of samples | 17 | 14 |
| Scores | | |
| 0 (no stain) | 0 | 7 |
| 1 (light stain) | 1 | 7 |
| 2 (dark stain in serial sections) | 16 | 0 |
| Fisher's 1-tail test on proportions | | |
| no. of successful trials | 17* | 7 |

*$p<0.05$
Differential expression of retrovirally-transfected β-galactosidase activity in bupivacaine-damaged and undamaged soleus muscle. From each muscle at least one sample of ten to thirty 16 um serial cross-sections were processed for the histochemical detection of β-galactosidase activity. The degree of β-galactosidase expression in each sample was scored according to the following system: 0, no activity; 1, occasional light diffuse or focal staining that does not necessarily appear in serial sections; 2, dark diffuse staining within the circumference of one or more fibers in serial sections. The Fisher's 1-tail test on proportions was performed (where scores of 1 and 2 were considered successful trials) and indicates a significantly greater β-galactosidase expression in the bupivacaine-damaged soleus muscle.

Example 3—In Vivo Retroviral Gene Incorporation in Rat Uterine Tissue

The following experiment was designed to examine the effectiveness of the presently described retroviral-mediated gene transfer system in mitotically-active uterine tissue of adult ovariectomized rats. Adult Sprague-Dawly female rats were ovariectomized under light ether anesthesia. The animals were then allowed to recover for a period of 7 days.

Following ovariectomy, the uterus of each animal was examined and found to have atrophied to the unstimulated state. The fully recovered ovariectomized rats with completely atrophied uterine tissue were then injected with estrogen at a dose of about 40 micrograms per Kg body weight (40 ug/mg B.W.). Upon estrogenic stimulation, the uterine tissue began to regenerate, with the attendant increase in cell proliferation.

Retroviral vectors including the β-galactosidase gene under the promoter control of the Moloney murine leukemia virus (MuLV) 5' long-terminal repeat were then injected into the uterine cavity and allowed to bath in the estrogen-treated uterus.

After a period of 18 hours, the treated animals were sacrificed. Uterine tissue samples were then fixed and examined microscopically as described in Example 1.

Results from this study indicate that the mitotically-active proliferating uterine cells of these adult female rats readily incorporated the β-galactosidase gene of the retroviral vector. This study also suggests the use of other hormones, such as testosterone, prostaglandins, prolactin, follicle stimulating hormone (FSH), human chorionic gonadotrophin (hCG), luteonizing hormone (LH), insulin, and other stimulatory hormones well known to those of skill in the art would be useful in the induction of a mitotically-active state in stimulating other cell types.

Example 4—Proposed Study for the In Vivo Regeneration of Dystrophic Muscle in Mice In this experiment, Applicants propose to demonstrate the integration and expression of a foreign reporter gene, β-galactosidase, in the replication-incompetent MoMuLV, into the DNA of replicating satellite cells of skeletal muscle in the dystrophic mouse. Applicants have already demonstrated that the described integration and expression can be achieved in adult normal rat skeletal muscle tissue, and therefore expect that the method will be successful in dystrophic mouse skeletal muscle tissue as well. This hypothesis is supported in the literature from observations that the regenerating capacity of young adult dystrophic muscles is almost equal to that of nondystrophic muscles.[19]

The ultimate application of the present methods in supplying dystrophic tissue with a foreign gene is to employ the method as a therapeutic corrective measure for the treatment of animals with genetic diseases, such as muscular dystrophy. In such an application, the retroviral vector will comprise a fragment of a dystrophin gene or a dystrophin gene construct.

In order to facilitate the inclusion of the required genetic information into a single retroviral vector, the dystrophin gene should comprise a dystrophin gene construct comprising a number of base pairs less than the 14,000 base pairs (14 kb) of the native dystrophin gene. Most preferably, this dystrophin gene construct comprises between about 10,000–8,000 base pairs of the native dystrophin gene. In a most preferred embodiment, the dystrophin gene construct comprises about 9,000 base pairs of the native dystrophin gene. This particular gene construct comprises a protein having a relative molecular weight of 200 Kd.

Recent studies have found that a very mild dystrophic phenotype was manifest in persons having only about 54% of the native dystrophin protein[20]. Thus, it is hypothesized that significant deletions may be made in the native dystrophin gene without a loss in essential biological function of the protein. Such a modified dystrophin gene is proposed for use in the dystrophin gene construct, as the "gene of interest", in the proposed retroviral vector of the presently claimed methods for treating human muscular dystrophy.

PHASE I

The following experiment is designed to determine if the integration and expression of the coding region for the rat insulin-like growth factor-I peptide in fibers of dystrophic muscle of mice will cause their hypertrophy.

| Experimental design Groups | Duration with retrovirus | |
|---|---|---|
| | 30 day | 180 day |
| dy/dy, mice without bupivacaine-retrovirus | 8* | 8 |
| dy/dy, mice with bupivacaine-retrovirus containing the coding region of insulin-like growth factor I | 8 | 8 |

*Number of mice

Chronology

Day 0: Injection of bupivacaine into soleus and anterior tibialis muscles

Day 2: Injection of replication-incompetent MoMuLV with insulin-like growth factor I into the 2-day Marcaine damaged, recovering muscles.

The treated designated muscles will then be removed and fixed as described previously.

Retrovirus description and handling

Applicants subcloned the insulin-like growth factor I coding region in the EcoRI site in the multiple cloning region of pT7/T3-18 (Bethesda Research Laboratories). The Sma I site in the multiple cloning region of pT7/T$^3$-18 and IGF-I has been converted to a PvuI by Sigma linker #L2392. Applicants plan to convert the EcoRI site at the 3' end of insulin like growth factor I to a BamHI site by usage of EcoRI-XmnI adaptor and BamHI-XmnI adaptor (New England Biolabs #1105 and 1106). Thus, the insulin-like growth factor I coding region will then have a 5' PvuI restriction site and a 3' BamHI restriction. Recall that β-galactosidase was removed by a 5' restriction at a PvuI site and a 3' restriction at a BamHI site, into which the insulin-like growth factor I will be subcloned.

The handling of the retrovirus, animal handling, and muscle sectioning are as described for Example 2. However, staining procedures as described for Example 2 will differ because there is no β-galactosidase gene in this particular replication-incompetent MoMuLV construct.

The following analyses will be made on serial sections of muscles:

1. Identification of fibers expressing insulin-like growth factor I will be made by either:
   a. In situ hybridization for insulin-like growth factor I mRNA, and/or
   b. Immunohistochemistry for neomycin phosphotransferase II.
2. Sizes of fibers with positive identification of either insulin-like growth factor I mRNA, or neomycin phosphotransferase vs size of fibers without expression in of the aforementioned.

In situ hybridization for insulin-like growth factor I mRNA will be performed, as described by Edwall, et al.[25] Applicants have obtained similar hybridization for the sense and antisense probes for IGF-I and are increasing the stringency to obtain preferential hybridization with the muscle IGF-I mRNA. For more specific localization of hybridization products, Applicants will employ $^3$H-labeled probes.

Biotinylated anti-neomycin phosphotransferase II will be obtained from 5'-3' (#5307-621261). Applicants are using biotinylated probes for in situ hybridization so there will be no difficulty with this detection system.

Neomycin phosphotransferase II is under constitutive expression by SV 40 early promoter region. Applicants have a JAVA image-processing software system which they use with a PC Vision Plus Frame Grabber Board in an AT-clone computer. Applicants use this system to determine the quantities of in situ hybridization, immunohistochemistry, and size of muscle fibers within serial sections.

PHASE II

Retroviral vectors will be prepared which include a dystrophin gene construct under the constitutive promoter control of the MoLV 5' long-terminal repeat. This dystrophin gene construct will comprise between about 10,000 and 8,000 base pairs of the native dystrophin gene, and encode a dystrophin protein having a relative molecular weight of 200,000. This particular gene fragment will be prepared as described by England et al.[20] In a most preferred embodiment, the dystrophin gene construct will comprise about 9,000 base pairs.

Dystrophic muscle of mice will then be treated with bupivacaine, as described above. The tissue will then be exposed to the described dystrophin-construct containing retroviral vector. Excision, fixation and analysis of the treated tissue of the dystrophic animals will then be performed as described in the previous examples.

Example 5—Proposed In Vivo Use in Human Gene Therapy of Muscular Degenerative Disease The gene encoding human dystrophin has been isolated as a "mammoth" gene, postulated to comprise 2.3 megabases. However, recent reports indicate the isolation of a segment of the native gene which has been demonstrated to impart to human subjects only mild dystrophic phenotypes[19]. Applicants propose the use of this "mini gene" together with the presently described and claimed retroviral mediated gene transfer system as applied to satellite muscle cells for the gene therapy of humans with genetic muscular degenerative diseases. These diseases include, by way of example, Duchenne's and Becker muscular dystrophies.

Use of the retroviral-mediated gene transfer systems described by the Applicants will effectively eliminate currently-recognized limitations in the art of gene therapy, such as the risk of immune rejection, diffusion, retroviral gene insert limitations and the requirement for multiple site injections (as in the case of myoblast injection to degenerative human muscle sites).

While the determination of exact treatment regimens for such a therapy await human in vivo clinical trials, it is hypothesized that the same pharmaceutical agents, radiation treatments, hormones, and other cell or tissue-discomposing events would elicit a mitotically-active state in human tissue and cells as they have in Applicants' experimental rats and mice. Current reviews suggest the process of muscle regeneration in humans shows few significant differences from the processes in mammalian experiments, saving those of scale due to the large size of human muscles, nor is there currently any reason to believe that the control mechanisms of muscle regeneration differ to any significant degree[5]. Thus, the successful gene incorporation accomplished with the techniques provided and described herein in rats are expected to be mimicked for the successful gene incorporation in humans.

The instant invention has been disclosed in connection with specific embodiments. However, it will be apparent to those skilled in the art that variations from the illustrated embodiments may be undertaken without departing the spirit and scope of the invention.

BIBLIOGRAPHY

The following documents in pertinent part are specifically incorporated herein by reference:
1. Gilboa, et al., (1986), *Biotechniques*, 4(6): 504–12.
2. Schultz, et al., (1985), *Mechanisms of Aging and Development*, 30:63–72.
3. Price, et al., (1987), *P.N.A.S.*, 84:156–60.
4. Ishiura, et al., (1986), *J. Cell Sci.*, 83:197–212.
5. Allbrook, D., (1981), *Muscle and Nerve*, 4:234–45.
6. McGeachie, et al., (1987), *Cell Tissue Res.*, 248:125–130.
7. Booth, F. W. (1989), *In: Biological Effects of Physical Activity*, 91–104
8. Dannenberg, et al., (1981), *In: Methods for Studying Mononuclear Plagocytes*, pp. 375–96.
9. Wigler, et al., (1977), *Cell*, 11:223–32.
10. Hwang, et al., (1984), *Mol, Cell Biol.*, 4:2289–97.
11. Williams, et al., (1984), *Nature*, 310:476–80.
12. Moore MAS, (1979), Stem Cell Concepts *In: Muscle Regeneration*, pp. 1–8.
13. Kantoff, et al., (1986), *Trans. Assoc. Am. Physicians*, 99:92–102.
14. Grounds, et al., (1987), *Cell Tissue Res.*, 250:563–569.
15. Benoit, et al., (1970), *J. Anat.*, 107:547–56.
16. Hall-Craggs, (1974), *Exp. Neurol.*, 43:349–58.
17. Partridge, et al., (1989), *Nature*, 337:176–9.
18. Anderson, et al., (1984) *Science*, 226:401–409.
19. Nonaka, et al., (1984), *Muscle and Nerve*, 11:400–7.
20. England, et al., (1990), *Nature*, 343:180–82.
21. Albrook, (1981), *Muscle and Nerve*, 4:234–45.
22. Karpati, et al., (1989), *A.J.P.*, 135(1):27–32.
23. Mandel, (1989), *Nature*, 339:584–6.
24. Love, et al., (1989), *Nature*, 339:55–8.
25. Edwall, et al., (1989), *Endocr.*, 124:820–25.
26. Fabrikant, J., (1987), *Health Physics*, 52(5):561–70.
27. Darr, et al., (1987), *J. Appl. Physiol.*, 63:1816–21.
28. Schultz, et al., (1985), *Mechanisms of Ageing and Development*, 30:63–72.
29. Greenberger, et al., (1988), *Int. J. Radiation Oncology Biol. Phys.*, 14:85–94.
30. Fisher, et al., (1988), *Radiation Research*, 113:40–50.
31. Slaga, et al., (1989) *The Cancer Bulletin*, (1):61–64.

What is claimed is:

1. A method for enhancing incorporation of a foreign gene into a tissue and expressing the incorporated foreign gene comprising:

inducing a mitotically-active state in a tissue in vivo to provide tissue with enhanced receptivity to the incorporation of a foreign gene;

preparing a retroviral vector capable of infecting a eucaryotic stem cell, said vector comprising a foreign gene; and injecting the tissue in vivo with the retroviral vector;

wherein said method results in incorporation and expression of the gene.

2. The method of claim 1, wherein the retroviral vector comprises a eucaryotic foreign gene.

3. The method of claim 1, wherein the foreign is a prokaryotic gene.

4. The method of claim 3, wherein the prokaryotic gene is a β-galactosidase gene.

5. The method of claim 1, wherein the foreign gene is a eucaryotic gene within a replication defective retroviral vector.

6. The method of claim 1 wherein a mitotically active state in a tissue is induced by treating the tissue with estrogen.

7. A method of retroviral injection into a tissue for the incorporation of a gene in a tissue comprising:

injecting the tissue with bupivacaine to induce a mitotically active state; and injecting the mitotically active tissue with a retroviral vector including the gene;

wherein said method provides efficient incorporation of the gene in the tissue.

8. The method of claim 7 wherein the tissue is muscle tissue.

9. The method of claim 7 wherein the tissue is uterine tissue.

10. The method of claim 7 wherein the retroviral vector is replication defective.

11. The method of claim 10 wherein the retroviral vector is a murine leukemia virus.

12. The method of claim 11 wherein the murine leukemia virus is Moloney murine leukemia virus.

13. The method of claim 7 wherein the foreign gene is a β-galactosidase gene.

14. A method for incorporating and expressing a foreign gene in a tissue comprising:

inducing a mitotically-active state in a tissue in vivo; and injecting the tissue in vivo with a retroviral vector, said retroviral vector including a foreign gene, wherein said foreign gene is efficiently incorporated in vivo in the tissue.

* * * * *

UNITED STATES PATENT AND TRADEMARK OFFICE
CERTIFICATE OF CORRECTION

PATENT NO. : 5,466,676,
DATED : November 14, 1995
INVENTOR(S) : Booth et al

It is certified that error appears in the above-indentified patent and that said Letters Patent is hereby corrected as shown below:

In claim 1, column 20, line 47, delete "in vivo" and insert
--*in vivo*--, therefor.

In claim 1, column 20, line 53, delete "in vivo" and insert
--*in vivo*--, therefor.

In claim 3, column 20, line 58, after "foreign", insert --gene--, therefor.

In claim 14, column 22, lines 9, 10 and 12, delete "in vivo" and insert --*in vivo*--, therefor.

Signed and Sealed this

Seventh Day of May, 1996

Attest:

BRUCE LEHMAN

*Attesting Officer*  Commissioner of Patents and Trademarks